United States Patent [19]

Terwilliger

[11] Patent Number: 5,449,001
[45] Date of Patent: Sep. 12, 1995

[54] BIOPSY NEEDLE

[76] Inventor: Richard A. Terwilliger, 3321 S. Rockwood La., Estes Park, Colo. 80517

[21] Appl. No.: 227,660

[22] Filed: Apr. 14, 1994

[51] Int. Cl.6 .............................................. A61B 10/00
[52] U.S. Cl. ................................................... 128/754
[58] Field of Search ......................... 128/751, 753, 754; 606/167, 170

[56] References Cited

U.S. PATENT DOCUMENTS

| | | | |
|---|---|---|---|
| Re. 34,056 | 9/1992 | Lindgren et al. | 128/754 |
| 4,600,014 | 7/1986 | Beraha | 128/754 |
| 4,699,154 | 10/1987 | Radiplast | 128/754 |
| 4,747,414 | 5/1988 | Brossel | 128/754 |
| 4,776,346 | 10/1988 | Beraha et al. | 128/754 |
| 4,817,631 | 4/1989 | Schnepp-Pesch et al. | 128/753 |
| 4,924,878 | 5/1990 | Nottke | 128/751 |
| 4,958,625 | 7/1990 | Bates et al. | 128/754 |
| 5,025,797 | 6/1991 | Baran | 128/754 |
| 5,183,052 | 2/1993 | Terwilliger | 128/753 |
| 5,188,118 | 2/1993 | Terwilliger | 128/753 |
| 5,220,926 | 6/1993 | Jones | 128/754 |
| 5,282,476 | 2/1994 | Terwilliger | 128/753 |

FOREIGN PATENT DOCUMENTS

| | | |
|---|---|---|
| 10321 | 10/1979 | European Pat. Off. . |
| 0141108 | 4/1980 | Germany . |
| 1551362 | 3/1990 | U.S.S.R. . |
| 83/03313 | 10/1983 | WIPO . |

*Primary Examiner*—Max Hindenburg
*Attorney, Agent, or Firm*—Fliesler, Dubb, Meyer & Lovejoy

[57] ABSTRACT

A biopsy needle including a stylet with a tissue collection notch formed in the shaft. The tissue collection notch is shaped in the form of a section of a circle in order to maximize the size of the tissue collected and to maximize the ability of the stylet to resist bending.

12 Claims, 5 Drawing Sheets

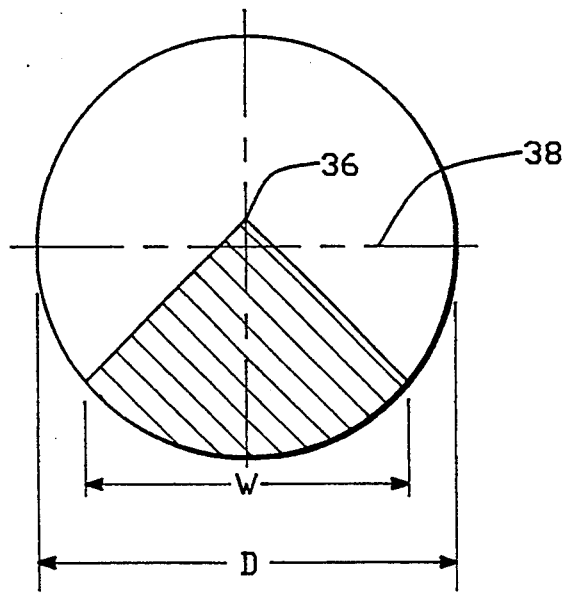
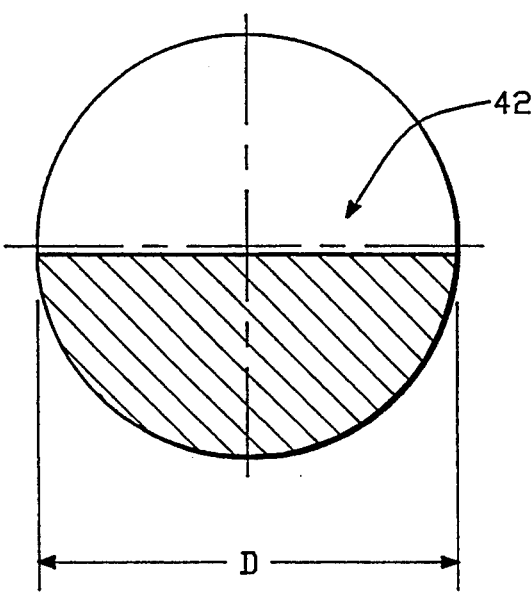
FIG.-3    FIG.-4
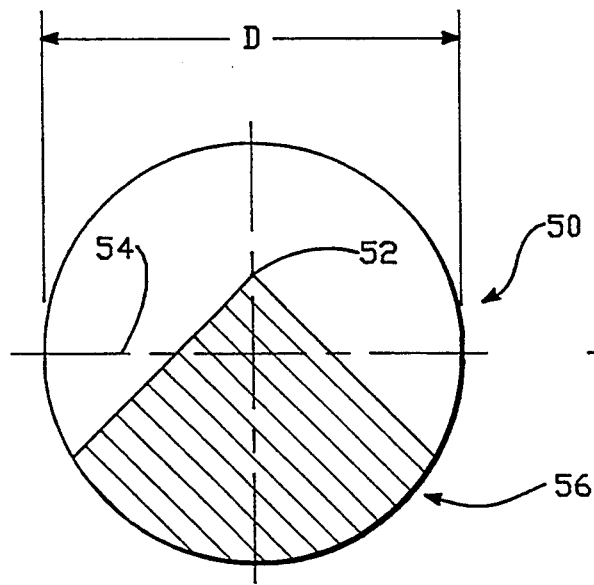
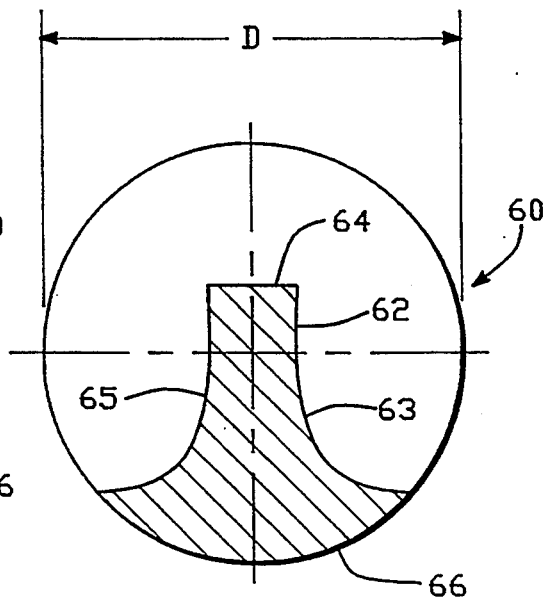
FIG.-9    FIG.-10

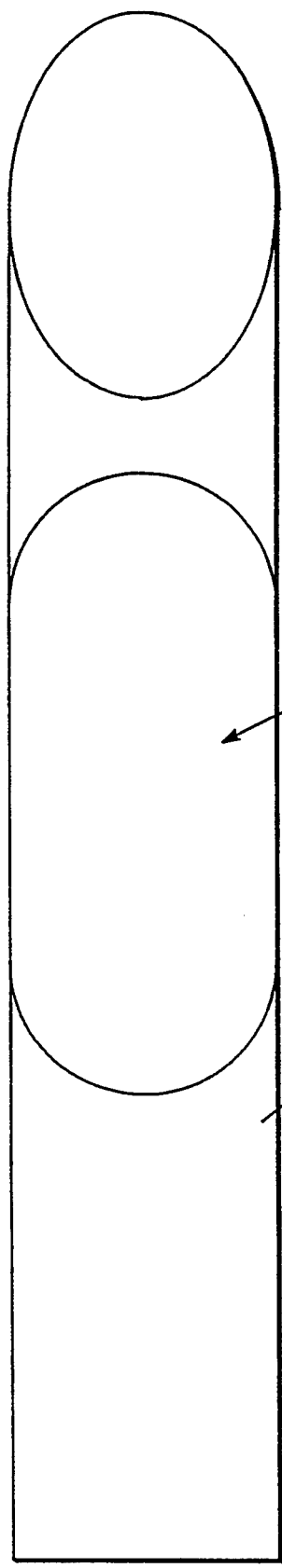
(PRIOR ART)
FIG.—5
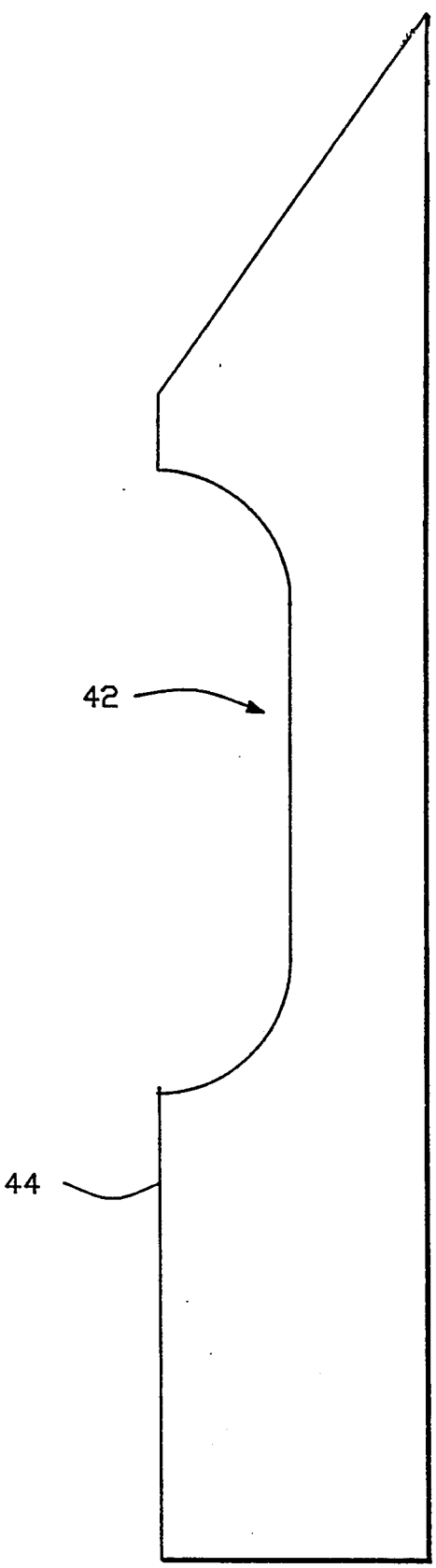
(PRIOR ART)
FIG.—6

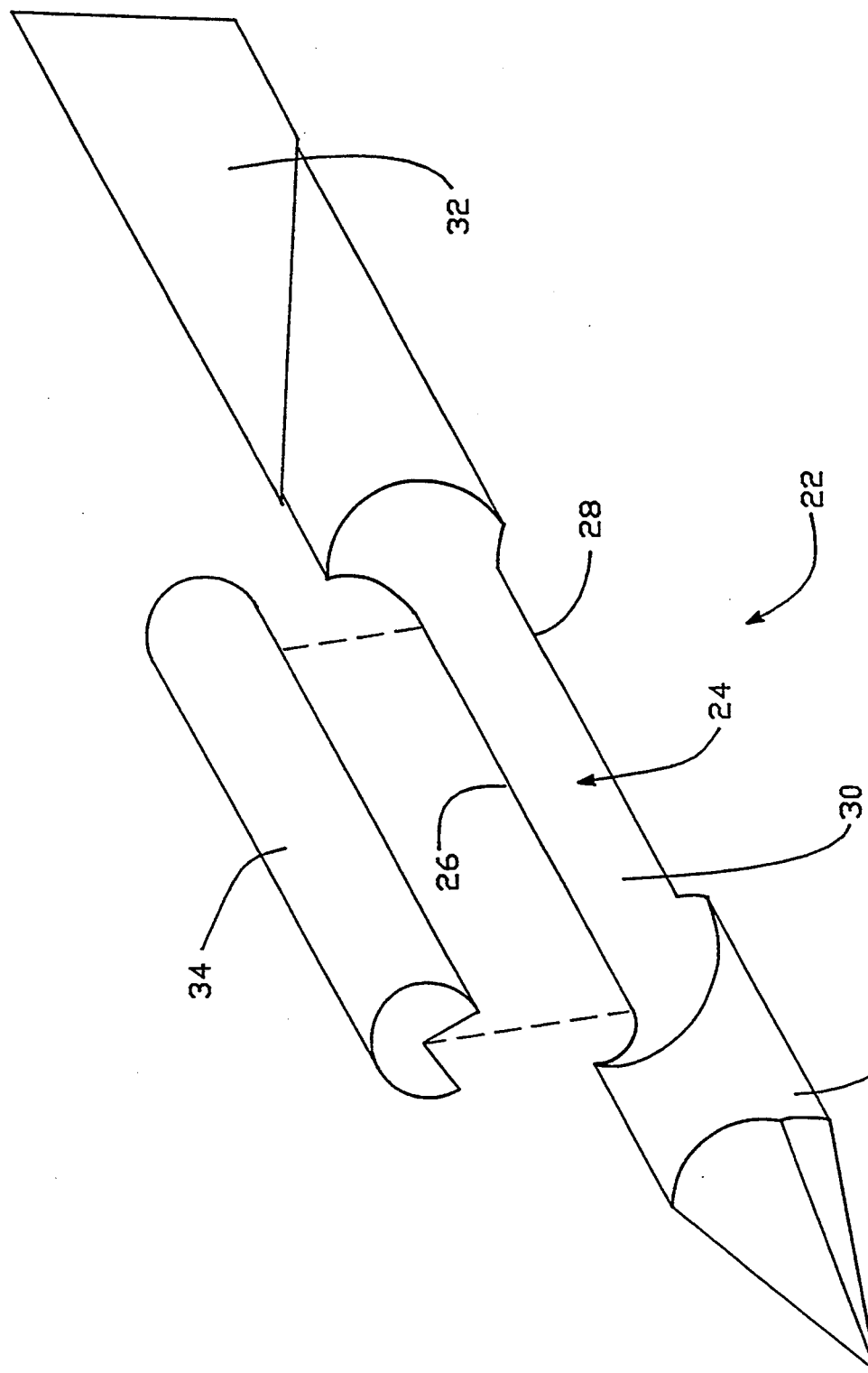
FIG.—8

BIOPSY NEEDLE

FIELD OF THE INVENTION

This invention relates to a new needle design to collect a tissue sample from humans or animals by a procedure referred to as tissue biopsy, and more particularly to an improved needle grind which can be used either manually or in automated biopsy instruments for performing the tissue extraction from a tissue mass in a precise manner for maximized tissue mass retrieval.

BACKGROUND OF THE INVENTION

It is often desirable and frequently absolutely necessary to sample or test a portion of tissue from humans and even animals to aid in the diagnosis and treatment of patients with cancerous tumors, premalignant conditions and other diseases or disorders. Typically in the case of cancer or the suspicion of malignant tumors, a very important process call tissue biopsy is performed to establish whether cells are cancerous.

Biopsy may be done by an open or closed technique. Open biopsy removes the entire tissue mass or a part of the tissue mass. Closed biopsy on the other hand is usually performed with a needle-like instrument and may be either an aspiration (hollow needle on a syringe) or a core biopsy (special tissue cutting needle design). In needle aspiration biopsy, individual cells or clusters of cells are obtained for cytologic examination. In core biopsy, a segment of tissue is obtained for histologic examination which may be done as a frozen section or paraffin section.

The methods and procedures of obtaining tissue samples for cytologic or histologic examination have been performed historically by manual insertion and manipulation of the needle. These procedures are performed "blind" by the physician and guided by "feel" and known anatomic "landmarks".

Tumors are first noted in a patient by one of three ways, palpation, X-ray imaging or Ultrasound imaging. Once a tumor is identified, a biopsy procedure is performed. Modern medical opinion dictates early detection of cancer increases the likelihood of successful treatment.

Two very important innovations in the field of medical technology have influenced the field of tissue biopsy in the last five years. One, the use of tissue imaging devices which allow the physician to "see" inside the body and visually guide the needle to the tumor mass. Two, The invention of Automatic Core Biopsy Devices (ACBD). The ACBD is an instrument which propels a needle set with considerable force and speed to pierce the tumor mass and collect the tissue sample. This ACBD device has allowed physicians to test tissue masses in the early stages of growth and has contributed to the medical trend of early diagnosis and successful treatment of cancer.

Examples of such ACBD devices have been described and used for obtaining tissue samples in U.S. Pat. Nos. 4,651,752; 4,702,260; and 4,243,048.

ACBDs have adapted the use of the manual Tru-Cut TM needle set developed by the Travanol company to obtain a "core" of tissue from the biopsy site. The Tru-Cut TM needle is comprised of an inner stylet with a semi-circular notch ground away at the distal end with an outer hollow cutting cannula. The stylet is advanced into the tissue and followed by the cannula which cuts and traps the tissue sample in the notch of the stylet. The Tru-Cut TM needle yields a core sample which is semi-circular in cross section with it's length determined by the length of the notch.

The stylet is the inner needle on the set with a notched cut out at the distal end. The cannula is the hollow needle of the set with an angled cutting surface at the distal end which slides over the stylet. When the stylet is pushed into tissue, the tissue is pierced and relaxes or prolapses into the notched cut out. When the cannula is slid forward, the tissue in the notch of the stylet is sliced off and retained in the notch until the cannula is drawn back.

The most common Tru-Cut TM needle sizes used for manual and ACBD applications are 18, 16 or 14 gauge with a sample length of 17 mm. The Tru-Cut TM set is limited to these sizes due to the design limitation of the cross-sectional material strength created by the grinding of the semi-circular notch. Use of the Tru-Cut TM needle design in smaller gauges or needles with longer notch lengths, would most likely cause bending or breaking of the stylet at the cross-section of the notch grind as the stylet entered the body. This potential bending or breaking would occur due to the forces created on entry and subsequent advancing of the stylet though the tissues of the body.

An additional limitation to the Tru-Cut TM needle design is its limited ability to allow tissue to prolapse into the notch at the time the stylet enters the biopsy site due to the geometry of the notch grind. The semi-circular notch grind across the approximate center line of the stylet diameter only allows prolapsing of tissue to occur from above the notch grind parallel to the notch surface. Since the grind occurs across the approximate centerline of the stylet diameter, tissue cannot prolapse into the notch detail from the sides of the notch, perpendicular to the ground surface. This limitation causes this design to have difficulty in obtaining adequate tissue in biopsy sites where the density of the tissue is very soft and in areas where the density is very stiff or hard without using large gauge needles such as 14 gauge.

This design limitation creates a situation of compromise between the physician's desire to use the smallest least invasive needle gauge and the pathologist's needs for as large a tissue sample as possible to minimize false-positive diagnosis.

The requirements of the physician and the pathologist dictates the need for an alternative approach in the function and design of the needle sets used in manual and ACBD devices. The ideal product would allow the use of smaller needle gages and/or longer samples required from a given biopsy site to obtain the necessary tissue required to make a diagnosis.

SUMMARY OF THE INVENTION

Accordingly it is a principle object of this invention to provide an improved needle design to more reliably obtain larger tissue samples which have an enlarged cross-section and/or notch length to provide more tissue mass for any given needle gauge.

It is a further object of this invention to provide a needle set with an improved notch grind geometry to obtain larger cores with more tissue mass.

It is a further object of this invention to provide a needle set with an improved notch grind geometry to enhance the ability to allow prolapsing of tissue into the notch grind.

It is a further object of this invention to provide a needle set with an improved notch grind geometry to enhance the cross-sectional strength of the notch grind to allow the use of smaller needle gauges and longer notch lengths without the possibility of bending or breaking.

It is a further object of this invention to provide a needle set which can be used in an ACBD instrument which accelerates a needle at such a velocity as to allow penetration of small tissue masses that would otherwise be too small to perform in closed biopsy.

It is another object of this invention to provide a needle set which can be used in an ACBD instrument which may be used to obtain multiple tissue samples from the same biopsy site.

These and other objects of the invention will be apparent from the following descriptions and claims.

Based on the prior art instruments for biopsy sampling of tissue masses and the actual present state of this art, there exists a need for a needle set which is capable of obtaining biopsy samples which yield more tissue volume for a given needle guage than currently marketed devices. This increased tissue volume allows the physician to use smaller needle gages and/or reduce the number of punctures per biopsy site.

The ability to use smaller needle gauges and/or less punctures per biopsy site, opens up the other major areas of biopsy procedures to the use of a device which will increase the reliability and safety of these procedures.

Accordingly I have invented a needle set for removing tissue samples of pre-determined size from a tissue mass which automatically penetrates and captures and allows the removal of said tissue sample for examination in one operation.

The needle set is an integral unit and consists of a outer hollow cannula and an inner pointed tipped stylet with a notch ground at the distal end. The stylet and the cannula are driven forward into the biopsy site in a defined motion in relation to each other.

In a preferred form, the stylet is the inner needle of the set with a notched cut out at the distal end. The cannula is the hollow outer needle of the set with an angled cutting surface at the distal end which slides over the stylet. When the stylet is pushed into tissue, the tissue is pierced and relaxes or prolapses into the notched cut out. When the cannula is slid forward, the tissue in the notch of the stylet is sliced off and retained in the notch until the cannula is drawn back.

The cross-sectional geometry of the notch grind is that of a section of a circle with an angle of approximately 90° in the preferred embodiment. The apex of this cross-section occurs at a point just above the centerline of the diameter of the stylet. This grind allows a tissue core to be obtained with an approximate cross-sectional area of 270°.

Because the cross-sectional geometry of the notch grind is less than 180°, the tissue surrounding the stylet on the sides of the notch can prolapse into the area of the stylet which is within the diameter of the needle thus allowing this tissue to be cut and captured by the cutting action of the cannula.

The stylet is a pointed needle positioned inside the cannula. The stylet may have a trocar pointed tip or other tip geometries, At the distal end of stylet, a pointed tip facilitates the introduction of the needles into the tissue mass. The stylet is positioned flush to the end of the cannula in the ready position. In the ready position the stylet prevents tissue from entering the cannula as the needle set is introduced into the body. As the stylet is advanced, the cannula remains stationary relative to the stylet, thus allowing the penetrated tissue to prolapse into the stylet notch before the cannula is motioned forward to cut and capture the tissue.

After removal from the biopsy site, the cannula is moved backwards over the stylet, exposing the tissue sample in the notch of the stylet. At this point the tissue sample can be removed from the needle set.

BRIEF DESCRIPTION OF THE DRAWINGS

The above noted advantages and other characteristic features of the present invention will be apparent from the accompanying drawings, and in part pointed out in the following detailed description of the preferred embodiment of the invention in which references will be made to the accompanying drawings wherein like reference numerals designate corresponding parts and wherein;

FIG. 3 is a cross-sectional view of the inventive notch grind geometry showing a plane perpendicular to the longitudinal axis of the stylet.

FIG. 4 is a cross-sectional view of the prior art notch grind geometry showing a plane perpendicular to the longitudinal axis of the stylet.

FIGS. 5 and 6 are top and side views of the distal end of the prior art stylet showing the notch grind geometry.

FIG. 8 is a perspective view of the inventive needle set with the stylet extended and a representative depiction of the tissue core sample obtained from this design.

FIGS. 9 and 10 depict cross sections of alternative notch designs of the invention.

DESCRIPTION OF THE PREFERRED EMBODIMENT

Figure 1:
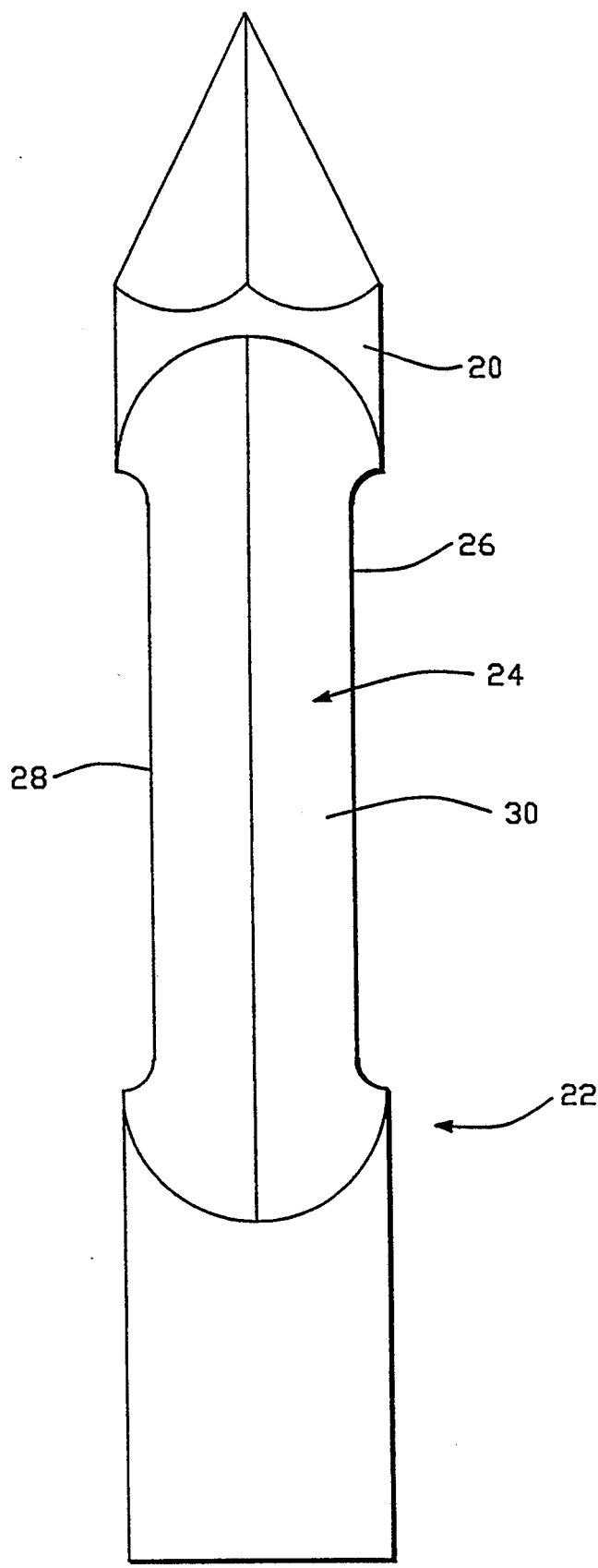
FIGS. 1 and 2 are top and side views of the distal end of the inventive stylet showing the notch grind geometry.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
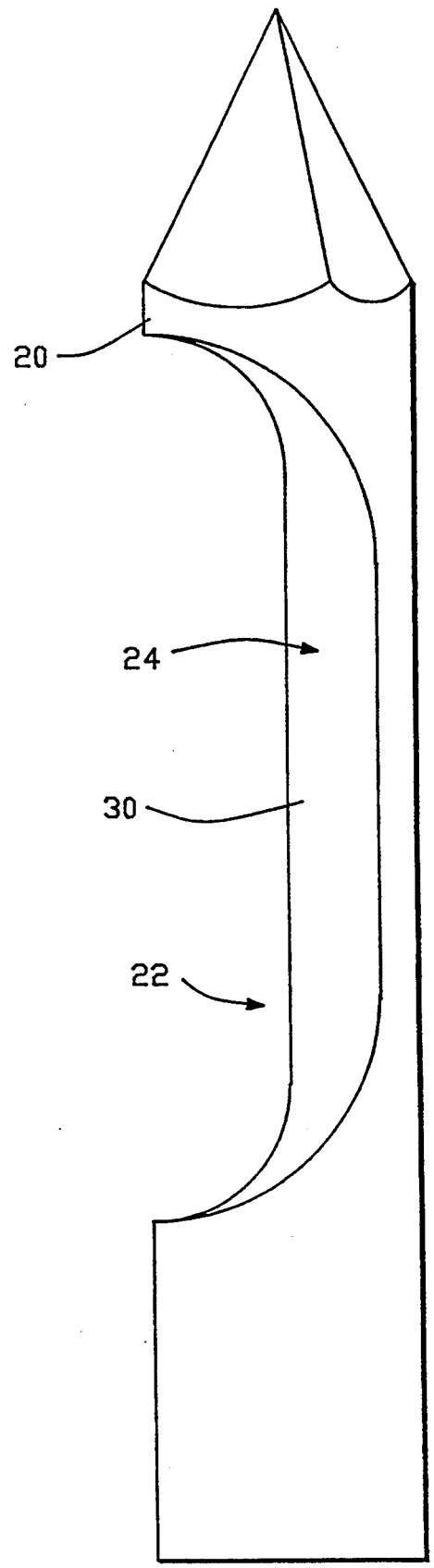

Considering now the drawings in detail:

FIGS. 1 and 2 show the top and side view of the distal end 20 of the inventive stylet 22. Note that in FIGS. 1 and 3, the needle grind geometry 24 removes material on the side regions 26, 28 of the notch 30 so that the notch width W is less than the overall diameter D of the stylet. This region where the material is removed allows surrounding tissue 34 (FIG. 8) to prolapse into the notch grind region 30 and thus allows the cannula 32 (FIG. 8) to cut and capture the tissue for removal.

FIG. 3 further illustrates that the needle grind geometry is approximately a section or sector of a circle with an angle of 90° this allows surrounding tissue to prolapse into the region where the cannula can cut and capture it, thus maximizing tissue yield. Due to the cross-sectional geometry of the needle grind, with the apex 36 just above the centerline 38 of the stylet diameter D, maximum strength is maintained preventing bending or breaking of the stylet 22 from the forces exerted during introduction into the biopsy site.

FIG. 4 illustrates the disadvantage of the prior art needle grind geometry 40. The notch grind 42 only removes material down to the point of the full needle diameter D or slightly below, thus preventing any substantial tissue prolapse in from the sides of the stylet. Any further grinding to a point below the maximum diameter D of the stylet 44 (FIG. 7) would increase the cross-section of tissue cut and captured but would so weaken the needle as to cause unwanted bending or breaking of the stylet.

FIGS. 5 and 6 show top and side views of the prior art illustrating the extent of the notch grind 42 and its effect on the width of the notch cross-section.

Figure 7:
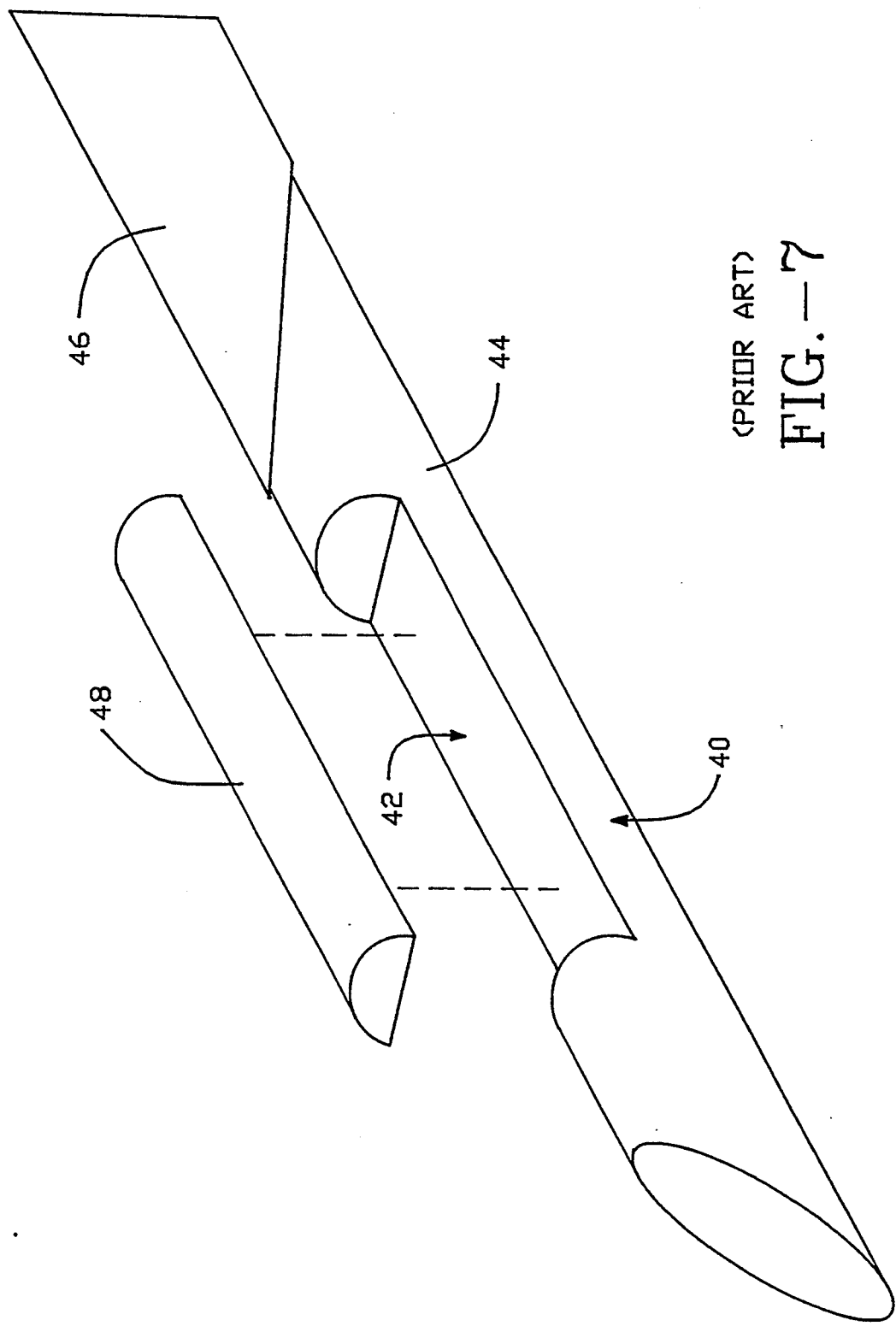
FIG. 7 is a perspective view of the prior art showing the needle set with the stylet extended and a representative depiction of the tissue core sample obtained from this design.

FIG. 7 is a pictorial illustration depicting the stylet 44 in its extended position after the stylet 44 has been extended and the cannula 46 has been urged forward to cut and capture tissue 46 in the notch. With the cannula retracted, FIG. 7 also shows a graphic representation of the tissue core shape obtained in this prior art design.

FIG. 8 is a pictorial illustration depicting the stylet 22 in its extended position after the stylet 22 has been extended and the cannula 32 has been urged forward to cut and capture tissue 34 in the notch 30. With the cannula 32 retracted, FIG. 8 also shows a graphic representation of the tissue core shape obtained in this inventive design.

FIG. 9 depicts an alternative notch design somewhat similar to FIG. 3. In FIG. 9 the needle grind geometry is a section of a circle with an angle less than 90 degrees. Due to the cross-section geometry of the needle grind 50, with the apex 52 above the centerline 54 of the stylet diameter D, maximum strength is maintained preventing bending or breaking of the stylet 56 from the forces exerted during introduction into the biopsy site.

FIG. 10 depicts yet another alternative design of the present invention. In this embodiment the needle grind geometry 60 has a tall central rail 62 with a flattened top 64. Rail expands downwardly and outwardly with curved sides 63,65 into a broad base 66 which covers in a preferred embodiment a circular segment of about 90 degrees. The top 64 of the rail 62 extends above the centerline 68 of the stylet diameter D. As can be appreciated by one of skill in the art, this embodiment and the other embodiments gain their resistance to bending in the same manner that an I-beam resists bending. That is to say that the major portions of the bending loads are carried by the top 64 and the bottom 66.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A stylet comprising:
   a shaft;
   a tissue collection notch formed in the shaft;
   said tissue collection notch shaped in cross-section in the form of a section of a circle whose included angle is less than 180°.

2. The stylet of claim 1 wherein:
   said sector describes an angle that is about ninety degrees.

3. The stylet of claim 1 wherein:
   said stylet has a diameter and said sector has an apex and wherein said apex is on the other side of a diametric line from the remainder of the sector.

4. The stylet of claim 3 wherein:
   said apex is flat.

5. The stylet of claim 1 wherein:
   said sector of a circle is shaped like an I beam.

6. A replacement needle set for a biopsy instrument including:
   a stylet;
   said stylet having:
      a shaft;
      a tissue collection notch formed in the shaft;
      said tissue collection notch shaped in cross-section in the form of a sector of a circle whose included angle is less than 180°;
   wherein said needle set is adapted to be secured to a biopsy instrument.

7. The replacement needle set of claim 6 including:
   a cannula;
   said cannula is positioned about said stylet and adapted to be secured to a biopsy instrument so that the instrument can move the cannula relative to the stylet in order to capture tissue in the notch of the stylet.

8. A stylet comprising:
   a shaft;
   a tissue collection notch formed in the shaft;
   said tissue collection notch in cross-section having a thinner portion upstanding from a broader base.

9. The stylet of claim 8 wherein:
   said thinner portion is in the form of a rail.

10. The stylet of claim 8 wherein:
    said broader base is formed along a segment of the outer periphery of the stylet.

11. The stylet of claim 8 wherein:
    said thinner portion is connected to the broader base by a central portion that curves inwardly.

12. The stylet of claim 8 wherein:
    said stylet has a diameter and said thinner portion is located on the other side of the diameter from the broader base.

* * * * *

UNITED STATES PATENT AND TRADEMARK OFFICE
CERTIFICATE OF CORRECTION

PATENT NO. : 5,449,001
DATED : September 12, 1995
INVENTOR(S) : Richard A. Terwilliger It is certified that error appears in the above-indentified patent and that said Letters Patent is hereby corrected as shown below:

Claim 1, Column 6, Line 10:
After the words "the form of a" and before the words "of a circle", delete the word "section" and insert therefor —sector—

Signed and Sealed this

Twentieth Day of February, 1996

Attest:

BRUCE LEHMAN

*Attesting Officer*   Commissioner of Patents and Trademarks